(12) United States Patent
Dold

(10) Patent No.: US 7,295,007 B2
(45) Date of Patent: Nov. 13, 2007

(54) REDUCING MOVEMENT ARTIFACTS IN MAGNETIC RESONANCE MEASUREMENTS

(75) Inventor: Christian Dold, Schoenwald (DE)

(73) Assignee: Fraunhofer-Gesellschaft zur Foerderung der Angewandten Forschung E.V. (DE)

( * ) Notice: Subject to any disclaimer, the term of this patent is extended or adjusted under 35 U.S.C. 154(b) by 272 days.

(21) Appl. No.: 11/010,431

(22) Filed: Dec. 14, 2004

(65) Prior Publication Data

US 2005/0137475 A1 Jun. 23, 2005

Related U.S. Application Data

(60) Provisional application No. 60/570,809, filed on May 14, 2004.

(30) Foreign Application Priority Data

Dec. 19, 2003 (DE) ................. 103 60 677

(51) Int. Cl.
*G01V 3/00* (2006.01)
(52) U.S. Cl. ..................... 324/307; 600/420
(58) Field of Classification Search ................ 324/307, 324/309; 600/420, 424, 426
See application file for complete search history.

(56) References Cited

U.S. PATENT DOCUMENTS

| 4,937,526 | A | | 6/1990 | Ehman et al. |
| 5,539,312 | A | | 7/1996 | Fu et al. |
| 5,545,993 | A | * | 8/1996 | Taguchi et al. ............. 324/309 |
| 6,096,048 | A | * | 8/2000 | Howard et al. ............. 606/130 |
| 6,421,551 | B1 | * | 7/2002 | Kuth et al. ................. 600/410 |
| 6,491,702 | B2 | * | 12/2002 | Heilbrun et al. ............ 606/130 |
| 2002/0118373 | A1 | | 8/2002 | Roshick et al. |
| 2003/0153826 | A1 | | 8/2003 | Grimm et al. |

FOREIGN PATENT DOCUMENTS

| DE | 199 09 816 | 3/1999 |
| WO | WO 00/28911 | 5/2000 |

OTHER PUBLICATIONS

PCT/ISA/210 PCT/EP99/08602.

* cited by examiner

*Primary Examiner*—Louis M. Arana
(74) *Attorney, Agent, or Firm*—Neifeld IP Law, PC

(57) ABSTRACT

An arrangement and a method for reducing movement artifacts in spatially resolved magnetic resonance measurements are proposed. A marker system which can emit or reflect at least one electromagnetic ray bundle is permanently connected to a measurement object. The electromagnetic ray bundles emanating from the marker system are projected by means of an imaging system onto spatially separated detector fields and movements of the measurement object are detected by means of the signals of the detector fields and by means of a triangulation method. A correction device generates a correction signal which correspondingly influences the magnetic resonance measurement. Also proposed is a marker system which has a mouthpiece and one or more hollow bodies which can reflect electromagnetic rays and are filled with a material which is visible during a magnetic resonance measurement.

13 Claims, 5 Drawing Sheets

REDUCING MOVEMENT ARTIFACTS IN MAGNETIC RESONANCE MEASUREMENTS

This application claims the benefit of U.S. Provisional application No. 60/570,809, filed 14 May 2004, the entire contents of which are incorporated herein by reference; and this application claims the benefit of German application DE 103 60 677.7, filed 19 Dec. 2003, the entire contents of which are incorporated herein by reference.

The invention relates to a method and an arrangement for correcting movement artifacts in spatially resolved magnetic resonance measurements. Such spatially resolved magnetic resonance measurements are used, in particular, for non-invasive structural elucidation in the field of material testing and in medical technology. An important example is provided by magnetic resonance tomography (MRT).

A movement of the object to be measured can lead to substantial problems with image quality in the case of spatially resolved magnetic resonance measurements. The reason for this is that individual pixels or image areas of the object to be measured are generally measured sequentially, that is to say by a sequential scanning of individual lines or planes of the object, for example. After recording has been done, the image information of the lines or planes are mostly combined in the computer to form a three-dimensional image. However, if the lines or planes are strongly displaced or tilted relative to one another because of a movement of the object to be measured, so-called movement artifacts are produced in the reconstructed image, that is to say losses of definition or structures not present in reality ("ghosts"). An undesired alteration of magnitude and phase corresponds to this in the spatial frequency domain.

The spatially resolved magnetic resonance measurement therefore fundamentally presupposes that the object to be measured is not moved appreciably in the volumetric region to be measured as scanning is being carried out. However, this presupposition is not fulfilled in many cases, since measurements necessarily have to be carried out on moving objects.

In the field of pharmacology, for example, it is of interest in many cases to determine with time resolution the propagation in the body of a test animal of specific active ingredients which are effectively visible in MRT. To date, the test animals have frequently been anaesthetized for this purpose in such a way that their movements are greatly limited.

This mode of procedure is, by contrast, not feasible in human diagnostics, where MRT recordings can sometimes last up to several hours. Particularly in the case of uncooperative patients such as children or elderly people, recordings are therefore frequently disturbed by spontaneous movements and need to be repeated. Furthermore, such measurements can be interrupted and subsequently continued only with difficulty, but this would be desirable in practice in the case of lengthy measurements.

It can be of interest in the field of material testing to investigate material fatiguing, for example, by means of magnetic resonance measurements on moving objects. This has been possible to date only for slow movements of low movement amplitude.

Various methods have been used to date in order to prevent or correct movement artifacts. One method which is used in several variations is the so-called navigator method which is disclosed in the documents U.S. Pat. Nos. 4,937,526, 5,539,312 and US 2003/0153826 A1. In these methods, a navigation measurement is inserted at regular intervals between the scans. In this navigator measurement, the position of the object to be measured, and the displacement or rotation of the object compared to the preceding navigator measurement are determined by means of various reference measurements. These reference measurements can be performed in various directions in the space of the wave vectors (k-space). Following the measurement, the data collected during the measurement are corrected computationally by means of the information from the navigator measurements. In the process, the data of each scan (for example the data of an image plane) are displaced and tilted in space by means of a coordinate transformation in accordance with the movements which the object has carried out during the measurement.

Various disadvantages occur in the navigator methods. A substantial disadvantage consists in that the reference measurements are time consuming and therefore substantially increase the duration of the overall measurement. Moreover, only relatively small movements of the object can be subsequently corrected with the aid of this method.

One known method by means of which movements of the object can be detected and corrected as early as during the measurement is described in US 2002/0118373 A1. The principle of laser triangulation is applied in this method, which is used, in particular, for functional MR tomography. Three laser diodes emit light rays onto a retroreflector in each case, from which the rays are retroreflected parallel to the respectively incident ray and are detected at the location or in the vicinity of the laser diodes. The reflected laser rays are detected using a line camera. Movements of the object can be detected and corrected in real time using this method.

However, various disadvantages also occur in this method. Thus, for example, converting the movement of the object calculated from the detector signals of the triangulation system into the absolute coordinate system of the MR tomograph is a complicated matter, since the exact position of the triangulation system is known only unsatisfactorily. Furthermore, the tolerance range for movements of the object is limited by the size of the retroreflectors. In addition, there is the risk that the retroreflectors fastened on the object, for example a patient's head, will slip or alter their position relative to the body volume, for example by movements of the scalp.

It is an object of the invention to specify a method and an arrangement which enable a reliable reduction or correction of movement artifacts in spatially resolved magnetic resonance measurements. The method is intended to permit real time tracking of the absolute position of the object in the coordinate system of the magnetic resonance apparatus. In particular, the invention is intended to permit high resolution MR image data to be obtained from objects where movements are critical (for example a head of a living vertebrate or human).

This object is achieved, in particular, by means of the inventive subject matter defined in the attached patent claims.

An arrangement and a method for reducing and/or correcting movement artifacts in spatially resolved magnetic resonance measurements are proposed. The arrangement has a magnetic resonance apparatus for spatially resolved magnetic resonance measurement having a region for accommodating a measurement object (sample space). This magnetic resonance apparatus can be, for example, an MR tomograph such as is used in medical technology. However, it can also be magnetic resonance apparatuses which are specifically designed for material testing.

The measurement can be performed in a spatially resolved fashion by means of the magnetic resonance apparatus.

Various options exist for this purpose. In commercially available MR tomographs, for example, signals from various locations of the measurement object which are frequency coded on the basis of a gradient of the magnetic field can be received simultaneously. The measurement object can be "scanned" in this way line by line or plane by plane, for example.

Other types of spatial resolution are also possible, however. Thus, for example, the measurement volume itself can be limited to a few cubic micrometers or cubic millimeters by suitable shaping of the magnetic field coils. In order to obtain information from various locations inside the measurement object, the latter is suitably displaced and/or rotated by means of a positioning device. Such devices can be used, in particular, for material testing.

Connected to the measurement object is a marker system which can emit at least one diverging electromagnetic ray bundle or can produce the ray bundle by reflecting incident electromagnetic rays. A marker system is understood as at least one marker together with fastening means, for example a mechanical holder, via which the marker system can be fastened on the measurement object. The marker can also be fixed by bonding, for example. The electromagnetic rays are typically light of one or more wavelengths from the infrared as far as into the ultraviolet spectral region. It is advantageous when a high percentage of the emitted or reflected radiation flux density of the ray bundle is situated in a narrow wavelength region (for example 90% within a wavelength region between 810 nm and 830 nm). Thus, in the case of reflection light of a defined wavelength is preferably irradiated in the direction of the marker system. The reflected or emitted ray bundle is preferably divergent, that is to say the ray bundle can simultaneously reach a plurality of detector fields which are arranged spaced apart from one another.

The marker system can be a system which has a dedicated light source (for example battery-operated light-emitting diodes or phosphorescent or chemiluminescent substances). On the other hand, it can also be a marker system which can reflect electromagnetic rays irradiated from outside.

The arrangement also has at least two spatially separated detector fields and one or more imaging systems. These detector fields are intended to render it possible in combination with the imaging systems to generate an item of information relating to the position and/or the alignment of the marker system. For example, these detector fields and the imaging systems can be cameras which record images of the sample space at regular or irregular intervals. The aim is that the light emitted or reflected by the marker system can be detected on these images such that the position of the marker system can be determined with the aid of image processing software, for example. This can be done, for example, in that the marker systems appear as bright spots on the images whose centroid can be determined automatically in each case.

Furthermore, the detector fields can also be other types of detectors, for example line cameras.

According to the method described, the marker system can produce an item of position information in each detector field. The spatial separation of the detector fields has the effect that at least two different items of position information are produced. A triangulation method known per se can be used to deduce the position of the marker system from the positions of the detector systems and the items of position information via the marker system. This calculation is performed in the proposed arrangement by means of a position determination device, for example an image processing system implemented on a personal computer.

If, in addition to the position of the measurement object, it is also intended to obtain an item of information relating to a spatial alignment, the marker system can, for example, have a number of spatially separated areas (markers) which reflect or emit electromagnetic rays. These spatially separated areas are also intended to be perceived by the detector fields in a spatially separate fashion, for example in the form of spatially separated light spots in the image of a camera. The position determination device is then used to determine separately the positions of the separated areas of the marker system. Depending on the number of these areas, it is then possible to determine not only the position of the marker system, but also its spatial alignment. As a rule, marker systems with three spatially separated areas are used in order to determine the position and the alignment of the measurement object in all spatial directions.

This determination of the position and/or alignment can be performed during and/or between sequences of the magnetic resonance measurement at different points in time, thus rendering it possible to detect a movement of the measurement object by means of a movement determination device (for example a personal computer). If it is established in this way that the measurement object has moved since the last determination of position or orientation (translation and/or rotation), the correction device can be used to generate a correction signal which correspondingly changes the mode of operation of the magnetic resonance apparatus. This correction device, for example a or the personal computer, can be configured to generate suitable movement correction signals in order to vary the magnetic field in the magnetic resonance apparatus (for example by adapting one or more magnetic field gradients). The next scan is then performed, for example, at a new measuring location, for example in a plane or along a line which is correspondingly adapted to the movement of the measurement object. Alternatively, in the case of magnetic resonance apparatuses having a positioning device (see above), it is also possible to adapt the position of the sample correspondingly, for example by translation or rotation.

The arrangement described offers the advantage that movements of the measurement object can be detected in real time or approximately in real time, that is to say as early as during the measurement, and so corresponding measures (correction of the measurement method or correction of the position of the measurement object) can be taken up immediately. The correction measures can also be carried out between two or more measurements.

For example, the information required for a complete investigation can be recorded in a number of sequences of the magnetic resonance measurement. A movement correction can be carried out during one sequence, between two sequences and/or after a few sequences. For example, a movement correction can be carried out during measurement processes of the magnetic resonance apparatus for the purpose of completing information in the spatial frequency domain (k space)—in particular, after respectively recording the information for a k space line—for example tracking the coordinate system of the magnetic resonance apparatus. This is particularly advantageous for long lasting measurements (for example 3D-echo sequences with high resolution of, for example, 512×512×512 k-space lines). The actual measurement must not be interrupted for this purpose. A subsequent correction of the data obtained is generally no longer required. However, it can nevertheless be performed in order to compensate geometrical distortions of the MR system, for example. It is also possible to make use in the process of the information relating to the movement of the measurement object obtained during the measurement.

Correction during measurement has great advantages in modern magnetic resonance apparatuses, in particular. A number of coils, also termed coil arrays, are used in such magnetic resonance apparatuses to read out the measurement information. The measurement resolution is substantially improved thereby. However, because of this measurement artifacts resulting from movement of the patient or object have a yet more disturbing effect than in the case of older magnetic resonance apparatuses, and an external tracking of movement becomes yet more important (and/or is advisable) in order to keep the measuring time as short as possible with regard to the clinical routine.

A particularly preferred embodiment relates to a magnetic resonance apparatus which has a measurement control device for controlling magnetic resonance measurements, and an evaluation device for evaluating measurement results of the magnetic resonance apparatus. The measurement control device is, for example, that unit of a magnetic resonance apparatus usually termed MCU (Measurement Control Unit). The evaluation device is, for example, that system of a magnetic resonance apparatus usually termed IRS (Image Reconstruction System). In particular, the measurement control device calculates that gradient of the magnetic field in the magnetic resonance apparatus which is required for the magnetic resonance measurements, as well as further controlled variables. From these, it generates the corresponding control signals with the aid of which the actual measurement devices (in particular the magnetic field coils) are driven. In order to carry out the measurement correctly, the measurement control device operates, for example, in real time, for example with a temporal accuracy of a few milliseconds for the control process.

In the past, in order to correct movements of the patient between the actual measurement sequences recorded, images were evaluated and the movement executed by the patient was calculated with the aid of contours. Subsequently, the evaluation device transmits the result of calculation to the measurement control device, which determines the required corrections therefrom.

In the particularly preferred embodiment, the measurement control device is connected (particularly not indirectly via an evaluation device, but directly) to the abovedescribed position determination device, which is combined with the marker system. The measurement control device receives directly from the position determination device (for example from a personal computer of the position determination device) movement signals which have information relating to the movement of the patient or object, the position determination device having determined information from the positions of the marker system. In particular, the information describes completely the movement of the patient or the object with regard to the six independent degrees of freedom of the movement. The measurement control device uses the movement signals to determine the required changes to the control signals with the aid of which the actual measurement devices are driven. For example, the information is stored in a data memory of the position determination device and continuously updated. The measurement control device can read out the information in this case via a defined interface (for example Ethernet interface).

A movement of the patient or the object can be corrected with the aid of this embodiment even when the measurement is running. Furthermore, the movement outside the measurement control device is possibly determined in conjunction with a large computational outlay, and so the precise timing of the control is not disturbed.

It has proved to be particularly advantageous when the marker system has reflecting properties. For this purpose, the marker system can have at least one marker which is configured to reflect electromagnetic rays. Reflection is to be understood in a general sense here as including scattering of the incident electromagnetic rays.

Furthermore, the arrangement can additionally have a source which is suitable for emitting an electromagnetic ray bundle in such a way that the marker system is reached by this ray bundle. In particular, the source is configured such that the entire region in which the marker system can move is illuminated.

This development offers the advantage that the marker system itself need have no source of electromagnetic rays (for example a light source), it thereby being possible to fashion the marker system simply in technical terms. A battery or similar energy source is not required.

Arrangements with one or more sources of electromagnetic waves can be used. These can be, for example, one or more infrared lamps.

The electromagnetic ray bundle(s) emitted by the source is/are reflected by the (preferably non-planar) surfaces of the marker system in such a way that the reflected electromagnetic ray bundles are in turn divergent and can therefore be detected simultaneously by a number of detector fields. A precise alignment of the detector fields and the imaging systems with the measurement object is not required.

It has proved to be particularly favorable when the marker system can additionally be detected by the magnetic resonance apparatus, that is to say when the position and/or alignment of the marker system with reference to the coordinate system of the magnetic resonance apparatus can be determined by one or more magnetic resonance measurements. It is possible in this way to set up a correlation between the position information of the detector fields and the coordinate system of the magnetic resonance apparatus by means of one or more reference measurements (for example at the start of or before a magnetic resonance measurement operation). The position information of the detector fields can thus be converted at any time into coordinates of the magnetic resonance apparatus by a simple coordinate transformation. This facilitates the correction of movement artifacts considerably (both online and subsequently).

It is proposed, in particular, additionally to determine the absolute position and/or alignment of the marker system in the coordinate system of the magnetic resonance apparatus, doing so by means of a spatially resolving magnetic resonance measurement. For example, in this way the origins and/or alignments of the coordinate systems of the marker system and of the magnetic resonance apparatus can be coordinated before starting a measurement of an object or subject. For example, the coordinate system of the marker system is adapted to the coordinate system of the magnetic resonance apparatus. By producing a fixed, known relationship between the coordinate systems of the marker system and the magnetic resonance apparatus, it is possible in every case (and this is proposed) to establish for a following measurement with the aid of the magnetic resonance apparatus a transformation rule (for example a transformation matrix) with which a movement (that is to say a movement of the object or subject) determined in the coordinate system of the marker system is transformed into a movement correction to be executed in the coordinate system of the magnetic resonance apparatus.

Particularly in the case of this transformation, it is preferred for a measurement device (for example a system of readout coils which produce a magnetic gradient field for reading out the measurement information) provided for determining the measurement information in the magnetic resonance apparatus to be driven in such a way that a measurement field (in particular the magnetic gradient field) produced by the measurement device has before and after the movement to be corrected the same position and/or alignment relative to the coordinate system of the marker system (and thus relative to the object or subject).

In order to set up a defined mutual relationship between the coordinate systems of the marker system and of the magnetic resonance apparatus, the marker system is preferably rendered "visible" to the magnetic resonance apparatus. It is expedient, in turn, when separated regions (markers) of the marker system can in this case be rendered visible separately in the magnetic resonance apparatus. It is thereby possible, in turn, to determine not only a position of the marker system, but also a spatial alignment of the marker system in the coordinate system of the magnetic resonance apparatus.

The marker system can, for example, be fashioned such that specific regions of the marker system are produced from a material which can be rendered visible with a high contrast in the magnetic resonance apparatus. In particular, this can be a proton-rich material (for example a hydrocarbon with a high density of hydrogen atoms, or water).

Movement artifacts can be largely, but generally not completely, eliminated by means of the arrangement described. Remaining losses of definition in the image information obtained by magnetic resonance tomography are frequently caused by the fact that the detector fields (for example cameras) have an image noise, or that vibrations have a negative influence on the quality of the position information.

These remaining losses of definition or movement artifacts can additionally be reduced by a development, a reference marker system being permanently connected to the magnetic resonance apparatus. The reference marker system is to be configured in such a way that it can, in turn, emit or reflect at least one electromagnetic ray bundle, the reference marker system advantageously being of similar or identical structural configuration to the marker system. The reference marker system is to be arranged in such a way that the position of the reference marker system can be determined by means of the detector fields.

Furthermore, the arrangement can have a noise correction device (for example an image processing system which is embodied by a personal computer) which is intended to correct or reduce apparent fluctuations in the determined position and/or alignment of the marker system connected to the measurement object which are not caused by the movement of the measurement object itself. This correction can be performed by determining the position and/or alignment of the reference marker system at the same time as determining the position and/or alignment of the marker system, or close to that time. Since the reference marker system does not, as a rule, vary its position and alignment in the coordinate system of the magnetic resonance apparatus, it is possible, nevertheless, to classify determined fluctuations in the position and/or alignment of the reference marker system as undesired noise or vibrations which are also simultaneously superimposed on the determined positions and/or alignments of the marker system. By simply forming the difference between the positions of the reference marker system and the positions of the marker system, such artifacts can be almost entirely eliminated, thus substantially raising the image quality.

A further advantageous refinement of the invention relates to the fashioning of a marker, in particular a marker for the abovedescribed marker system. This marker system can, in particular, have one or more hollow bodies having a cavity for use as marker. The hollow body is configured in such a way that it has at least one material surrounding the cavity and reflecting electromagnetic rays. The marker can be, for example, a hollow ball (for example with a centered cavity).

The material reflecting electromagnetic rays which surrounds the cavity must not form the wall of the cavity. Rather, it is also possible to arrange a further material between the reflecting material and the cavity. In particular, it is possible for only the surface of the hollow body to reflect the radiation.

The reflecting material is to have reflecting properties for the irradiated electromagnetic rays. It is particularly advantageous when infrared radiation is involved here and, for example, the surface of the hollow body has a high reflectivity in this wavelength region (for example at 820 nm).

Furthermore, the cavity of the hollow body is preferably filled with a material which can be detected by a magnetic resonance measurement. As described above, this can be, for example, a hydrocarbon with a high proton density and/or water which has been doped in order to raise the proton density.

Alternatively, or in addition, however, it is also possible to use other liquids which can be detected in the MR tomography.

Fastening the marker system on the measurement object frequently poses a considerable technical problem. In particular, with spatially resolved magnetic resonance measurements on vertebrates or humans this fastening must be performed such that even a displacement of the skin relative to the muscle tissue or skeleton does not exert a negative influence on the determination of position.

Particularly when examining the head, it has proved to be particularly advantageous in this context when the marker system has a mouthpiece configured for placing inside the mouth, and a fastening device to be placed outside the mouth, the fastening device and the mouthpiece being permanently connected to one another. At least one marker (for example a marker in one of the abovedescribed refinements) can be fastened on the fastening device of the marker system, and can emit or reflect at least one electromagnetic ray bundle. This can be, for example, an arrangement of three of the abovedescribed hollow bodies. These hollow bodies are to be arranged on the fastening device in such a way that they are spaced apart from one another. In this way, they can be perceived by the detector fields with sufficient spatial separation, and their positions can therefore be effectively determined. In particular, the hollow bodies should not be arranged in a line, thereby rendering it possible to determine the alignment of the marker system of all three spatial directions.

Fastening in the mouth of the vertebrate or patient ensures effective fixing of the marker system relative to the cranial bone and brain, which is particularly advantageous in recordings of the head region. With vertebrates and non-cooperative patients (for example elderly patients or children), the mouthpiece to be placed inside the mouth can additionally be fastened by means of underpressure on the palate or jaw. The durability of the positioning of the marker system can be further improved with the aid of this painless fixing.

Suitable mouthpieces are marketed, for example, by Medical Intelligence GmbH, Feyerabendstrasse 13-15, 86830 Schwabmuenchen, Germany.

In addition to the described arrangements and the method, the scope of the invention includes a computer program which when running on a computer or computer network executes those parts of the method according to the invention entirely or partially in one of its refinements which relate to driving the participating devices and/or processing the information obtained.

Also belonging to the scope of the invention is a computer program having program code means for carrying out entirely or partially those parts of the method according to the invention which relate to driving the participating devices and/or processing the information obtained when the program is being run on a computer or computer network. In particular, the program code means can be stored on a computer-readable data carrier.

Also belonging to the scope of the invention is a data carrier on which a data structure is stored which, after loading into a main memory of a computer or computer network, can execute entirely or partially those parts of the method according to the invention which relate to driving the participating devices and/or processing the information obtained.

Also belonging to the scope of the invention is a computer program product having program code means, stored on a machine-readable carrier, in particular, for carrying out entirely or partially those parts of the method according to the invention which relate to driving the participating devices and/or processing the information received when the program is being run on a computer or a computer network.

In this case, a computer program product is taken to be the program as a commercially available product. It can be present in principle in any desired form, such as, for example, on paper or on a computer-readable data carrier and can, in particular, be distributed over a data transmission network.

The invention is explained in more detail below with the aid of exemplary embodiments which are illustrated diagrammatically in the figures. However, the invention is not restricted to the examples. Identical reference numerals in the individual figures can in this case denote elements which are identical or functionally identical or correspond to one another with regard to their functions. In detail:

Figure 1:
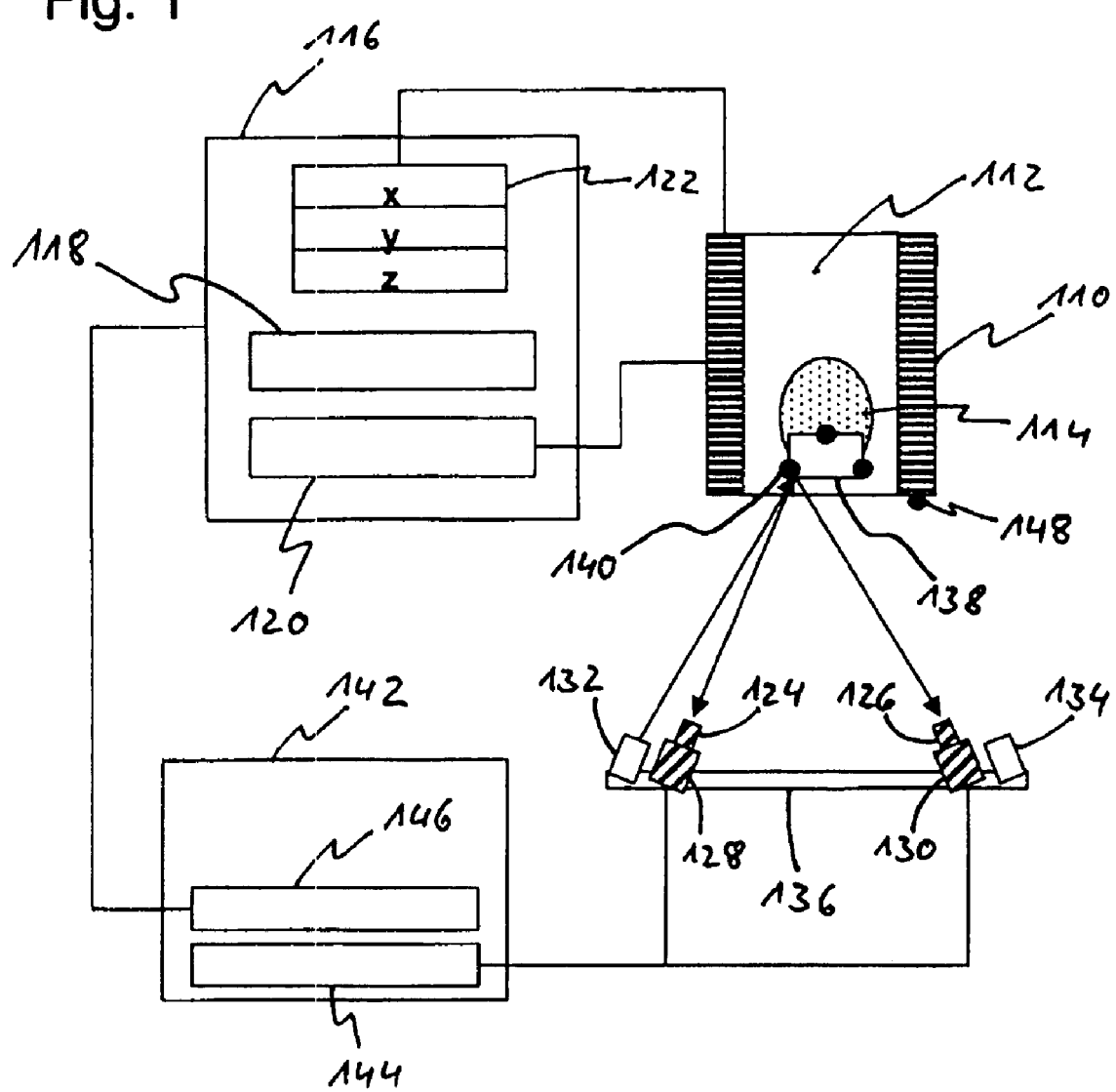
FIG. 1 shows a top view of an arrangement for correcting movement artifacts of magnetic resonance measurements by means of a camera system, an illumination system and image processing as well as of a marker system.

FIG. 1 shows a preferred refinement for reducing movement artefacts. A magnetic resonance apparatus 110 for spatially resolved magnetic resonance measurements has a sample space 112 for accommodating a measurement object 114 (illustrated diagrammatically as a head, in this case). A Siemens Magnetom 3T Whole Body System manufactured by Siemens Medical System GmbH is used as magnetic resonance apparatus in this case.

The magnetic resonance apparatus is connected to an electronic controller 116 which has a central control unit 118, a measurement data acquisition system 120 and a measurement positioning device 122.

Two digital camera systems 128, 130 equipped with suitable infrared objectives 124, 126, and two diffuse infrared light sources 132, 134 are fixed on a positioning rail 136. The positioning rail is installed at a distance of four meters from the center of the magnetic field coils, where a magnetic field of 10 mT remains to be entered only. This measure is required so that the magnetic forces on components of the camera systems do not cause damage to or maladjustment of the arrangement. Screened cables are used in order to reduce negative effects of the magnetic fields on the data signals of the camera systems.

A marker system 138 is fixed on the measurement object 114, the marker system having three markers 140 provided with an infrared-reflecting surface. The camera systems 128, 130 and the light sources 132, 134 are aligned such that the markers 140 are located in the image field of the camera systems 128, 130 and in the light cone of the light sources 132, 134.

The camera systems 128, 130 are connected to a personal computer 142 which has an image processing system 144 and a central processing unit 146. The personal computer 142 is connected to the electronic controller 116.

During the magnetic resonance measurement (for example after recording of each image plane during MR tomography or at specific time intervals during the recording of an image plane), the position of the markers 140 is determined with the aid of the image processing system 144. For this purpose, the objectives 124, 126 are used to project onto the CCD chips of the digital camera systems 128, 130 the light emitted by the diffuse infrared light sources 132, 134 and reflected by the markers 140. The image processing system 144 therefore registers the markers 140 as bright spots in the image area and can determine the position of the markers 140 in the respective coordinate system of the camera systems 128, 130, for example by determining the centroid of the bright spots. It follows that the spatial direction from which each marker 140 appears, viewed from each camera system 128, 130 is known.

A conventional triangulation method is now used to determine the absolute position of the markers 140 in space. Starting from each camera system 128, 130, a virtual straight line is drawn in the spatial direction in which the marker appears, viewed from the respective camera system. The position of the marker 140 is yielded by the point of intersection of these straight lines and from the known position of the camera systems 128, 130. If the position and the angular position of the cameras 128, 130 are not precisely known, the determination of position can also be calibrated by means of a reference measurement on a reference marker system (not illustrated in FIG. 1).

Once the positions of all three markers 140 of the marker system 138 have been determined in this way, the position and alignment of the measurement object 114 is adequately determined for this instant. In order further to raise the accuracy of the measurement of the position and the alignment of the marker system 138, use may be made of a reference marker system 148 permanently connected to the magnetic resonance apparatus 110. Artifacts which are not produced by movements of the measurement object 114 (but by noise, vibrations etc) can be avoided or reduced by comparing the measured position and alignment of the marker system 138 with the measured position and alignment of the reference marker system 148.

If the positions and the alignments of the marker system 140 have changed between two measurements (for example before and after the MR scan of a plane of the measurement object 114), this can easily be determined by means of the described arrangement. Suitable correction measures can consequently be taken up. This is performed by the central processing unit 146 converting the change in the position and alignment of the measurement object 114 into suitable correction signals for the electronic controller 116 of the magnetic resonance apparatus 110, and passing them on to it.

The central control unit 118 of the electronic controller 116 correspondingly corrects the drive of the measurement positioning device 122, for example by change in the drive parameters for the coil currents of the magnetic field coils. The next MR scan of a plane of the measurement object 114 is then undertaken using the corrected drives such that the movement of the measurement object 114 is compensated. The spatial resolution can be improved by up to 0.1 mm using this method.

Similarly, the correction can also already be undertaken during an MR scan, and this further improves the accuracy of the measurements and the reduction of movement artifacts.

Figure 2:
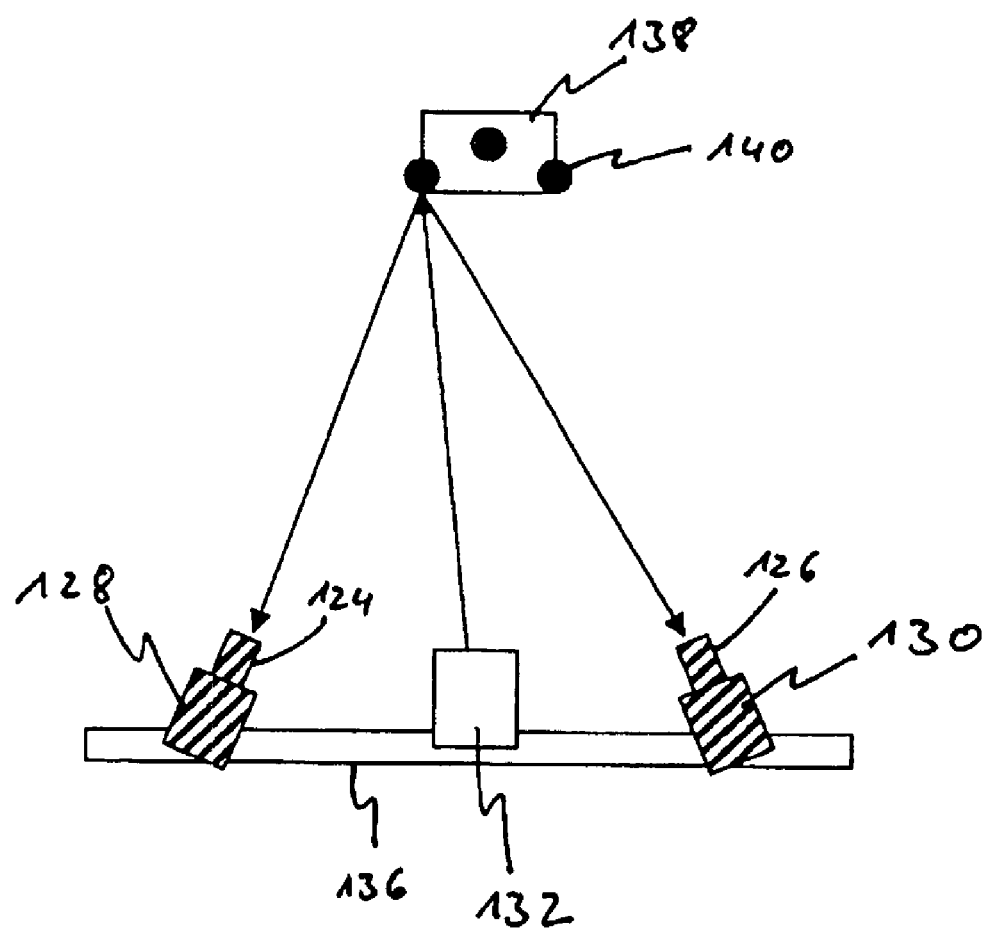
FIG. 2 shows a top view of an arrangement which is an alternative to FIG. 1 and has an individual diffuse light source.

A variation of the setup illustrated in FIG. 1 is depicted in FIG. 2. Use is made in this setup of only one diffuse infrared light source 132, which is arranged on the positioning rail 136 in the middle between the two camera systems 128, 130. In this way, the arrangement can be of more compact design than the arrangement illustrated in FIG. 1.

Figure 3:
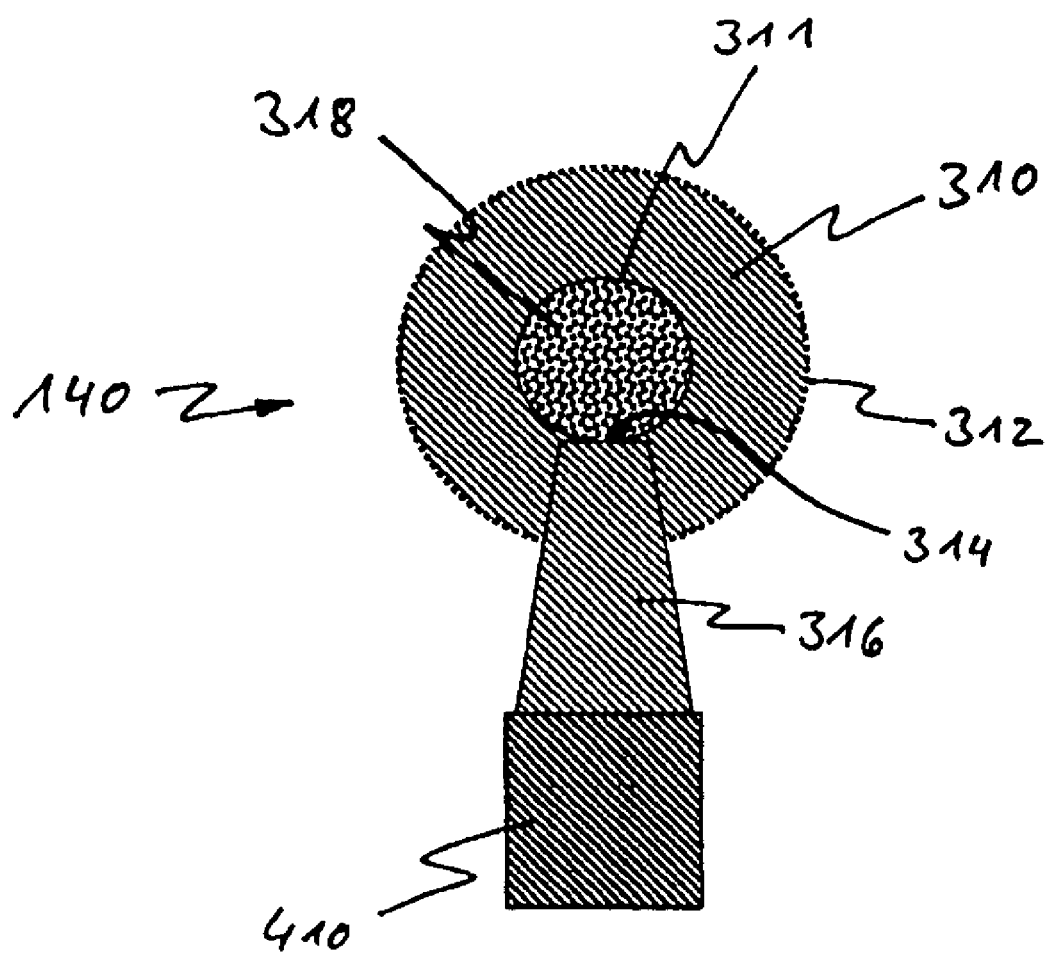
FIG. 3 shows a hollow body with a curved, reflecting surface and, as marker, a filling of a material visible in the magnetic resonance measurement.

A marker 140 corresponding to a preferred setup is illustrated in FIG. 3. The marker has a spherical hollow body 310 with a cavity 311 which is produced from plastic (polyethylene in this case). The surface 312 of the hollow body 310 is formed by an outer layer (in particular a varnish layer) which exhibits high reflection in the infrared spectral region.

The hollow body has a filling opening 314 which is closed by a plastic stopper 316 in fluid tight fashion during operation of the marker. As is illustrated in FIG. 3, the plastic stopper can also be used to connect the hollow body 310 to a fastening device 410. The cavity 311 of the hollow body 310 is filled with water 318 of high proton density.

Figure 4:
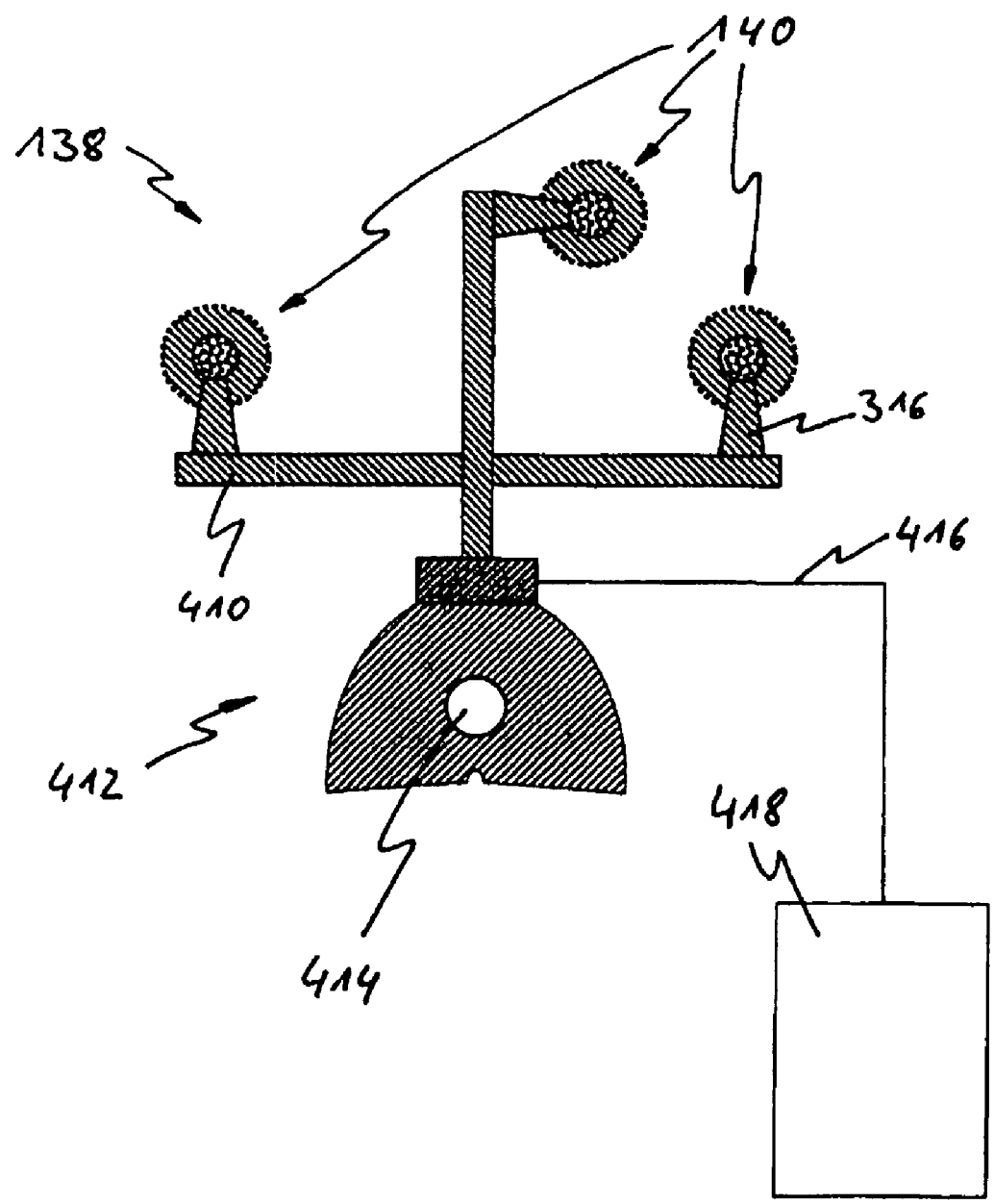
FIG. 4 shows a marker system, which can be fixed by means of a vacuuming device, having a mouthpiece.

The way in which the markers 140 depicted in FIG. 3 can be connected to form a marker system 138 is illustrated in FIG. 4. Three markers 140 are connected via their plastic stoppers 316 to a cruciform fastening device 410. The fastening device 410 is connected to a mouthpiece 412. The mouthpiece has a row of suction openings 414 which are connected to a vacuum pump 418 via a vacuum line 416.

The marker system 138 is fixed by the patient taking the mouthpiece 412 into his mouth, where it is sucked onto the palate by vacuum with the aid of the suction openings 414, and thereby fixed.

Figure 5:
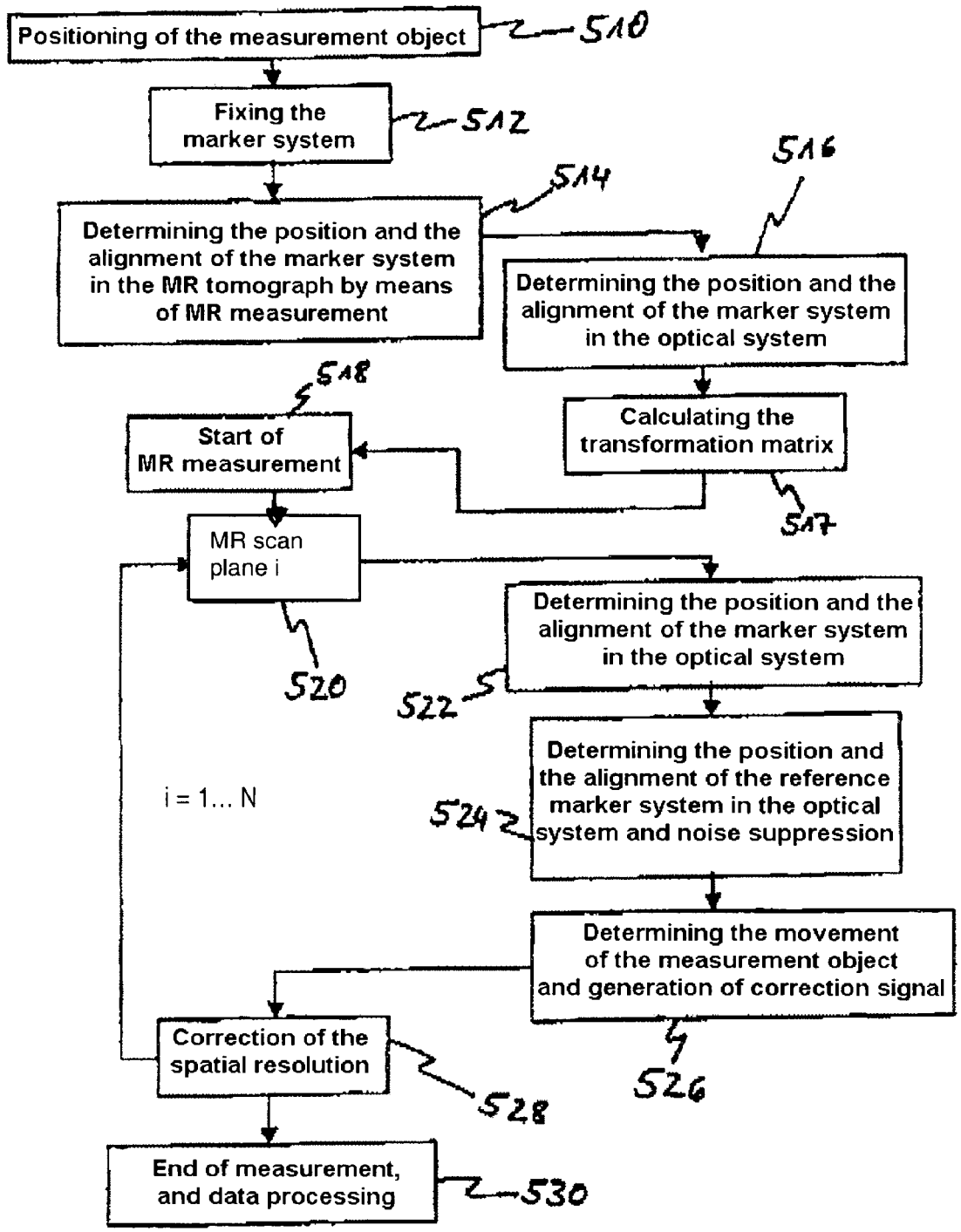
FIG. 5 shows a flowchart of a refinement of the method according to the invention.

FIG. 5 illustrates a preferred configuration of the method for correcting and/or reducing movement artifacts, as a flowchart. In a first step 510, the measurement object 114 is positioned, that is to say, for example, a patient is positioned on a spatially adjustable couch, or a test setup is positioned with moveable parts for testing, this being done inside the sample space 112 of the magnetic resonance apparatus 110.

In step 512, a marker system 138 is permanently connected to the measurement object 114. This is to be a marker system 138 which has markers 140 which can be rendered visible by means of magnetic resonance measurements. In the next step 514, it is therefore possible to determine the position and the alignment of the marker system 138 in the coordinate system of the magnetic resonance apparatus 110 by means of a spatially resolved magnetic resonance measurement.

Subsequently, the position and the alignment of the marker system 138 is determined in the coordinate system of the cameras 128, 130 in step 516 by means of the optical system described in FIG. 1. In step 517, the position and alignment of the marker system 138 in the coordinate system of the MR tomograph and in the coordinate system of the optical system 128, 130 is used to calculate the transformation matrix, which converts the two coordinate systems into one another.

The spatially resolved magnetic resonance measurement is then started in step 518, in this case by starting the first MR scan in step 520.

After termination of the MR scan of the first image plane, the position and the alignment of the marker system 138 in the optical system is then carried out anew in step 522. A measurement of the position and the alignment of the reference marker system 148 is carried out here at the same time (step 524). As described above, this information is used to suppress artifacts as a consequence of noise or vibrations.

A possible movement of the measurement object is determined in step 526 from the information, obtained in steps 522 and 524, relating to the position and alignment of the measurement object 114, and a correction signal is correspondingly calulated therefrom for the positioning of the next scan. As described above, this correction signal is then converted in the electronic controller 116 of the magnetic resonance apparatus 110 in a correction of the spatial resolution.

This method, including the correction of the spatial resolution, is repeated a total of N times, N constituting the number of image planes. The tomography is concluded in step 530 after measurement of the Nth image plane, and the data processing is started.

REFERENCE NUMERALS

110 Magnetic resonance apparatus
112 Sample space
114 Measurement object
116 Electronic controller
118 Central control unit
120 Measurement data acquisition system
122 Measurement positioning device
124 Objective
126 Objective
128 Digital camera system
130 Digital camera system
132 Diffuse infrared light source
134 Diffuse infrared light source
136 Positioning rail
138 Markersystem
140 Marker
142 Personal computer
144 Image processing system
146 Central processing unit
148 Reference marker system
310 Hollow body
311 Cavity
312 Surface of the hollow body 310
314 Filling opening
316 Plastic stopper
318 Water filling
410 Fastening device
412 Mouthpiece 414 Suction opening
416 Vacuum line
418 Vacuum pump
510 Positioning of the measurement object
512 Fixing of the marker system
514 Determining the position and the alignment of the marker system in the MR tomograph
516 Determining the position and the alignment of the marker system in the optical system
517 Calculating the transformation matrix
518 Starting the MR measurement
520 Mr-Scan of the ith image plane
522 Determining the position and the alignment of the marker system in the optical system
524 Determining the position and alignment of the reference marker system in the optical system and noise suppression
526 Determining the movement of the measurement object, and generating a correction signal
528 Correction of the spatial resolution
530 Termination of the measurements and commencement of the data processing

What is claimed is:

1. An arrangement for reducing movement artifacts in images of an object obtained from spatially resolved magnetic resonance measurements, comprising:
a magnetic resonance apparatus adapted for producing spatially resolved magnetic resonance measurement of a measurement object;
a marker system comprising at least one source and at least one marker, wherein said marker system is adapted to emit from said at least one source at least one diverging electromagnetic ray bundle and to produce at least one diverging electromagnetic ray bundle by reflecting from said at least one marker electromagnetic rays produced by said at least one source, and wherein said marker system is adapted to be firmly connected to the measurement object;
at least two spatially separated detector fields;
at least one imaging system for imaging a portion of said at least one diverging electromagnetic ray bundle impinging the detector fields;
a position determination device for calculating at least one of position and alignment of said marker system from signals of the detector fields;
wherein said arrangement is also designed to determine position and alignment of said marker system from spatially resolved magnetic resonance measurement of said at least one marker;
wherein said arrangement is also designed to determine a correlation between position and alignment of said marker system obtained from said signals of the detector fields and position and alignment of said marker system obtained from said spatially resolved magnetic resonance measurement of said at least one marker, thereby enabling a coordinate transformation of the position and alignment information from a coordinate system of the detector fields to a coordinate system of the in the magnetic resonance apparatus;
a movement determination device for determining at least one of position and alignment of the measurement object from said at least one of position and alignment of said marker system; and
a correction device for generating a movement correction signal for driving the magnetic resonance apparatus.

2. The arrangement of claim 1, wherein the at least two detector fields are arranged so that rays of the at least one diverging ray bundle which emanates from the marker system can simultaneously reach a plurality of the detector fields and wherein the detector fields are arranged spaced apart from one another.

3. The arrangement of claim 1, wherein the marker system comprises a hollow body having a cavity;
the hollow body comprises at least one material surrounding the cavity, which material is adapted to reflect electromagnetic rays; and
the cavity of the hollow body is filled with a material which can be detected by a magnetic resonance measurement.

4. The arrangement of claim 1, further comprising:
a reference marker system which is adapted to reflect at least one electromagnetic ray bundle and which is firmly connected to the magnetic resonance apparatus; and
a noise correction device for correcting apparent fluctuations, which are not caused by movement of the measurement object, in at least one of the position and alignment of the marker system, which is connected to the measurement object.

5. The arrangement of claim 1, wherein the correction device is configured to generate movement correction signals which vary a magnetic field in the magnetic resonance apparatus.

6. A method of using a marker system for reducing movement artifacts in images of an object obtained from spatially resolved magnetic resonance measurements on a vertebrate or human, comprising:
adapting the marker system to emit at least one diverging electromagnetic ray bundle by reflecting electromagnetic rays and wherein the marker system can be firmly connected to a measurement object of a magnetic resonance measurement;
wherein the marker system comprises a mouthpiece configured for placing inside a mouth of the vertebrate or human and comprises a fastening device which is connected to the mouthpiece and which is to be placed outside the mouth;
wherein at least one marker, which is adapted to reflect at least one electromagnetic ray bundle, is fastened on the fastening device; and
correlating between (1) position and alignment of said marker system obtained from signals generated by parts of said at least one diverging electromagnetic ray bundle impinging at least two spatially separated detector fields and (2) position and alignment of said marker system obtained from said spatially resolved magnetic resonance measurement by a magnetic resonance apparatus of said marker system, thereby enabling a coordinate transformation of the position and alignment information from a coordinate system of the detector fields to a coordinate system of the magnetic resonance apparatus.

7. The method of using the marker system according to claim 6, wherein the marker system comprises as the marker three hollow bodies, each having a cavity;
each of the hollow bodies comprises at least one material surrounding the cavity, which material is adapted to reflect electromagnetic rays; and
the cavity of the hollow body is filled with a material which can be detected by the magnetic resonance measurement.

8. The method of using the marker system according to claim 6, wherein the mouthpiece is adapted to be fastened by means of under pressure on a palate or jaw of the vertebrate or human.

9. A method for reducing movement artifacts in images of an object obtained from spatially resolved magnetic resonance measurements, comprising:

produceing with a marker system at least one electromagnetic ray bundle by reflecting electromagnetic rays, wherein said marker system is firmly connected to a measurement object;

recording images of the marker system at various angles of view;

obtaining from said images information relating to at least one of a translational and a rotation of the measurement object;

correlating between (1) position and alignment of said marker system obtained from said images and (2) position and alignment of said marker system obtained from spatially resolved magnetic resonance measurement by a magnetic resonance apparatus of said marker system, thereby enabling a coordinate transformation of the position and alignment information from a coordinate system of the detector fields to a coordinate system of the magnetic resonance apparatus; and carrying out a movement correction during the magnetic resonance measurements between magnetic resonance measurements by using the information.

10. The method of claim 9, wherein a divergent electromagnetic ray bundle is irradiated in direction of the marker system; and a portion of the ray bundle is reflected by the marker system.

11. The method of claim 9, wherein at least one of an absolute position and alignment of the marker system in a coordinate system of said magnetic resonance apparatus is determined by a spatially resolving magnetic resonance measurement.

12. The method of claim 9, wherein information relating to at least one of a position and an alignment of a reference marker system, which is firmly connected to a magnetic resonance apparatus, is obtained;

apparent fluctuations, which are not caused by the movement of the measurement object, in the position the alignment of the marker system, are determined from this information; and the apparent fluctuations are taken into account in the movement correction.

13. The method of claim 9, wherein at least two detector fields are arranged spaced apart from one another; and each of the detector fields detects information sufficient to produce one of the images of the marker system.

* * * * *

UNITED STATES PATENT AND TRADEMARK OFFICE
CERTIFICATE OF CORRECTION

PATENT NO. : 7,295,007 B2  Page 1 of 1
APPLICATION NO. : 11/010431
DATED : November 13, 2007
INVENTOR(S) : Dold It is certified that error appears in the above-identified patent and that said Letters Patent is hereby corrected as shown below:

Column 13, line 58, replace:

"the in the magnetic resonance apparatus;"

with the following:

--the magnetic resonance apparatus;--

Signed and Sealed this

Twenty Second Day of April, 2008

JON W. DUDAS
*Director of the United States Patent and Trademark Office*